(12) United States Patent
Kimura et al.

(10) Patent No.: US 10,524,802 B2
(45) Date of Patent: Jan. 7, 2020

(54) HEMOSTATIC DEVICE

(71) Applicant: TERUMO KABUSHIKI KAISHA, Shibuya-ku, Tokyo (JP)

(72) Inventors: Ayako Kimura, Shizuoka (JP); Teppei Hayashi, Bear, DE (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 281 days.

(21) Appl. No.: 15/723,544

(22) Filed: Oct. 3, 2017

(65) Prior Publication Data
US 2018/0042615 A1 Feb. 15, 2018

Related U.S. Application Data

(63) Continuation of application No. PCT/JP2016/060984, filed on Apr. 4, 2016.

(30) Foreign Application Priority Data

Apr. 7, 2015 (JP) ................................ 2015-078481

(51) Int. Cl.
*A61B 17/135* (2006.01)
*A61B 17/132* (2006.01)

(52) U.S. Cl.
CPC ........ *A61B 17/135* (2013.01); *A61B 17/1322* (2013.01)

(58) Field of Classification Search
CPC .............. A61B 17/135; A61B 17/1325; A61B 17/1322; A61B 2017/00455; A61B 2017/00907

See application file for complete search history.

(56) References Cited

U.S. PATENT DOCUMENTS 3,654,931 A * 4/1972 Hazlewood .......... A61B 17/135
 606/202
5,649,954 A * 7/1997 McEwen .............. A61B 17/135
 600/490
5,690,610 A * 11/1997 Ito ....................... A61F 13/0203
 602/46

(Continued)

FOREIGN PATENT DOCUMENTS

JP 10-005058 U 4/1935
JP 11-512630 A 11/1999

(Continued)

OTHER PUBLICATIONS

International Search Report (PCT/ISA/210) dated Jun. 21, 2016, by the Japanese Patent Office as the International Searching Authority for International Application No. PCT/JP2016/060984.

(Continued)

*Primary Examiner* — Phong Son H Dang

(74) *Attorney, Agent, or Firm* — Buchanan Ingersoll & Rooney PC

(57) ABSTRACT

A hemostatic device has a flexible band that can be wrapped around a hemostasis-requiring site of a limb, a securing portion that secures the band in a state where the band is wrapped around the limb, and an inflation portion that interlocks with the band, and that inflates when a fluid is injected. The inflation portion has a plurality of convex portions in a width direction orthogonal to a longitudinal direction of the band when the inflation portion inflates.

19 Claims, 15 Drawing Sheets

(56) References Cited

U.S. PATENT DOCUMENTS

| | | | |
|---|---|---|---|
| 6,336,901 B1* | 1/2002 | Itonaga | A61B 5/02141 600/499 |
| 6,811,535 B2* | 11/2004 | Palti | A61B 5/02233 600/499 |
| 6,932,773 B2* | 8/2005 | Inoue | A61B 5/02233 600/485 |
| 7,498,477 B2* | 3/2009 | Wada | A61B 17/1325 602/53 |
| 8,481,803 B2* | 7/2013 | Wada | A61B 17/1325 602/53 |
| 8,481,805 B2* | 7/2013 | Wada | A61B 17/1325 602/53 |
| 8,524,974 B2* | 9/2013 | Wada | A61B 17/1325 602/53 |
| 8,759,603 B2* | 6/2014 | Wada | A61B 17/1325 602/53 |
| 8,870,781 B2* | 10/2014 | Lee | A61B 5/021 600/485 |
| 9,332,994 B2* | 5/2016 | Pancholy | A61B 17/1325 |
| 9,895,155 B2* | 2/2018 | Wada | A61B 17/1325 |
| 9,936,959 B2* | 4/2018 | Wada | A61B 17/1325 |
| 9,949,741 B2* | 4/2018 | Wada | A61B 17/1325 |
| 10,058,334 B1* | 8/2018 | Wada | A61B 17/1325 |
| 10,219,809 B2* | 3/2019 | Wada | A61B 17/1325 |
| 10,390,839 B2* | 8/2019 | Benz | A61B 17/1325 |
| 2002/0170359 A1* | 11/2002 | Yamakoshi | A61B 5/02141 73/756 |
| 2002/0188315 A1* | 12/2002 | Guzman | A61B 17/135 606/203 |
| 2004/0098035 A1* | 5/2004 | Wada | A61B 17/1325 606/201 |
| 2009/0138039 A1* | 5/2009 | Wada | A61B 17/1325 606/202 |
| 2010/0081977 A1 | 4/2010 | Vess | |
| 2012/0221041 A1* | 8/2012 | Hansson | A61B 17/1325 606/203 |
| 2013/0116725 A1* | 5/2013 | Wada | A61B 17/1325 606/202 |
| 2013/0178894 A1* | 7/2013 | Wada | A61B 17/1325 606/202 |
| 2013/0245674 A1* | 9/2013 | Wada | A61B 17/1325 606/202 |
| 2013/0245675 A1* | 9/2013 | Wada | A61B 17/1325 606/202 |
| 2013/0282048 A1* | 10/2013 | Wada | A61B 17/1325 606/202 |
| 2013/0289613 A1* | 10/2013 | Wada | A61B 17/1325 606/202 |
| 2013/0331752 A1 | 12/2013 | Vess | |
| 2015/0018869 A1* | 1/2015 | Benz | A61B 17/135 606/203 |
| 2015/0327869 A1* | 11/2015 | Harren | A61B 17/12 606/201 |
| 2015/0335334 A1* | 11/2015 | Pancholy | A61B 17/1325 606/202 |
| 2016/0174952 A1* | 6/2016 | Shah | A61B 17/0057 606/213 |
| 2016/0213373 A1* | 7/2016 | Drasler | A61B 17/1325 |
| 2016/0338709 A1* | 11/2016 | Wada | A61B 17/1325 |
| 2016/0338710 A1* | 11/2016 | Nakamoto | A61B 17/1325 |
| 2018/0000491 A1* | 1/2018 | Wada | A61B 17/1325 |
| 2018/0000492 A1* | 1/2018 | Wada | A61B 17/1325 |
| 2018/0000493 A1* | 1/2018 | Wada | A61B 17/1325 |
| 2018/0000494 A1* | 1/2018 | Wada | A61B 17/1325 |
| 2018/0008283 A1* | 1/2018 | Hazama | A61B 17/135 |
| 2018/0014833 A1* | 1/2018 | Wada | A61B 17/1325 |
| 2018/0042615 A1* | 2/2018 | Kimura | A61B 17/135 |
| 2018/0228496 A1* | 8/2018 | Wada | A61B 17/1325 |

FOREIGN PATENT DOCUMENTS

| | | |
|---|---|---|
| JP | 2000-225119 A | 8/2000 |
| JP | 2008-119517 A | 5/2008 |
| JP | 2013-039471 A | 2/2013 |
| WO | WO 2014/095646 A1 | 6/2014 |

OTHER PUBLICATIONS

Written Opinion (PCT/ISA/237) dated Jun. 21, 2016, by the Japanese Patent Office as the International Searching Authority for International Application No. PCT/JP2016/060984.

* cited by examiner ic Device

CROSS-REFERENCE TO RELATED APPLICATIONS

This application is a continuation of International Application No. PCT/JP2016/060984 filed on Apr. 4, 2016, which claims priority to Japanese application number 2015-078481 filed on Apr. 7, 2015, the entire contents of which are incorporated herein by reference.

TECHNICAL FIELD

The present invention relates to a hemostatic device for performing hemostasis by compressing a punctured site.

BACKGROUND ART

In recent years, treatment and inspection have been percutaneously performed by introducing an introducer sheath into a punctured site of a blood vessel in an arm or a leg and inserting a catheter into a lesion area of the blood vessel via a lumen of the introducer sheath. In a case where this method is employed, it is necessary to perform hemostasis at the puncture site after the introducer sheath is removed. In order to perform the hemostasis, a known hemostatic device is used, which includes a band for being wrapped around the puncture site of the arm or the leg, a securing portion for securing the band in a state where the band is wrapped around the puncture site, and an inflation portion which inflates so as to compress the puncture site when a fluid is injected (for example, refer to JP-A-2008-119517). The hemostatic device performs the hemostasis by directly applying a compressive force generated from the inflation portion to the puncture site.

According to such a hemostatic device, the inflation portion inflates and presses the puncture site. Thus, the inflation portion continuously compresses a blood vessel or a nerve for a long time. Consequently, in some cases, numbness or pain may be caused, or the blood vessel may be occluded. Therefore, in order to adjust pressure applied to the puncture site by the inflation portion, a doctor or a nurse performs an operation for decompressing the inflation portion, thereby reducing the compressing force acting on the puncture site with the lapse of time.

Hemostatic performance achieved by compressing the puncture site is in a trade-off relationship with the pain or numbness caused by compressing the blood vessel or the nerve. Accordingly, there is a need for a hemostatic device that can further relieve the pain or numbness while still sufficiently performing the hemostasis on the puncture site.

SUMMARY

The disclosure herein is directed to a hemostatic device which can sufficiently perform hemostasis at a puncture site while relieving pain caused by the compressive force of an inflation portion. Specifically, the hemostatic device according to the disclosure here relieves the pain caused by the inflation portion in such a way that the inflation portion applies dispersed pressure to the puncture site and minimizes stress on a punctured wound.

In order to achieve the same, the disclosure provides a hemostatic device having a flexible band that can be wrapped around a hemostasis-requiring site of a limb, a securing portion that secures the band in a state where the band is wrapped around the limb, and an inflation portion that interlocks with the band, and that inflates when a fluid is injected. The inflation portion has a plurality of convex portions which are aligned with each other in a width direction orthogonal to a longitudinal direction of the band when the inflation portion inflates.

According to the hemostatic device of the disclosure herein, when the inflation portion inflates, the inflation portion includes the plurality of convex portions which are aligned with each other in the width direction of the band. Therefore, when the band is wrapped around the limb, the convex portions of the inflation portion are disposed so as to be aligned with each other in an extending direction of a hemostasis-requiring blood vessel. Therefore, the hemostatic device according to the disclosure can cause the convex portions to apply a dispersed compressive force to a plurality of locations on the blood vessel, when the inflation portion inflates. That is, the hemostatic device according to the disclosure can cause the inflation portion to apply the dispersed compressive force to the plurality of locations in the blood vessel. Accordingly, the hemostatic device can perform hemostasis while suppressing pain occurrence as much as possible.

The hemostatic device may include a marker for aligning the inflation portion with the hemostasis-requiring site. In this manner, the hemostatic device causes the marker to align with a puncture site, thereby enabling the inflation portion to compress a desired position on a body surface. Therefore, the hemostatic device according to the disclosure herein can restrain blood leakage caused by misalignment of the inflation portion, and can reliably perform the hemostasis at the puncture site.

The marker may be disposed between the adjacent convex portions. In this manner, the hemostatic device causes the marker to align with the puncture site, thereby enabling the puncture site to be pinched between two convex portions when the inflation portion inflates. Hence, the hemostatic device according to the disclosure herein can compress the puncture site by pinching both an upstream side and a downstream side of the puncture site of the blood vessel. Accordingly, the hemostatic device can restrain the convex portions from excessively compressing the puncture site. In this manner, the hemostatic device can achieve an excellent hemostatic effect while relieving pain. Note that, in a case of an artery, the upstream side of the blood vessel means a direction closer to the heart of the blood vessel. In addition, the downstream side of the blood vessel means a direction away from the heart of the blood vessel.

The marker may be eccentrically disposed on one side in the width direction of the band. In this manner, the hemostatic device causes the marker to align with the puncture site. Accordingly, when the inflation portion is disposed at the puncture site, it becomes easy to set the compressive force applied to the upstream side of the blood vessel to be stronger than that applied to the downstream side of the blood vessel. Therefore, the compressive force applied to the upstream side of the blood vessel, which is closer to the heart and has a higher blood pressure, can be stronger than the compressive force applied to the downstream side of the blood vessel. Accordingly, it is possible to achieve an excellent hemostatic effect while the stress or burden on a living body is reduced as much as possible without excessively inhibiting a blood flow.

The hemostatic device may have a curved plate formed of a material harder than that of the band, and the band may be configured to hold the curved plate so as to overlap the inflation portion. In this manner, if the hemostatic device causes the inflation portion to inflate after a user wears the hemostatic device, the curved plate restrains the inflation portion from inflating in a direction away from the body surface of the limb, and thus, the compressive force of the inflation portion concentrates on the hemostasis-requiring blood vessel. Therefore, the hemostatic effect is improved, and it is possible to avoid a possibility of compressing other blood vessels or nerves which do not require the hemostasis. Accordingly, it is possible to inhibit the occurrence of hand numbness or poor blood circulation. In addition, since the curved plate is curved, the compressive force of the inflation portion can be effectively received by the curved plate. Accordingly, an excellent hemostatic effect can be achieved by effectively adjusting the compressive force applied to the limb.

The hemostatic device may also have a pressing member that presses the inflation portion between the curved plate and the inflation portion, and the pressing member may be disposed so as to overlap the inflation portion. In this manner, a hemostatic member can cause the pressing member to adjust a direction in which the inflation portion applies pressure to the puncture site. Therefore, a hemostatic effect is improved, and it is possible to avoid a possibility of compressing other blood vessels or nerves which do not require the hemostasis. Accordingly, it is possible to inhibit the occurrence of hand numbness or poor blood circulation.

BRIEF DESCRIPTION OF THE DRAWINGS

FIG. 6(A) is a front view of the inflation portion when viewed from a wearing surface side, and FIG. 6(B) is a side view of the inflation portion when viewed in a direction along the wearing surface.

FIG. 7(A) is a front view of the inflation portion when viewed from the wearing surface side, and FIG. 7(B) is a side view of the inflation portion when viewed in the direction along the wearing surface.

FIG. 8(A) is a front view of the inflation portion when viewed from the wearing surface side, and FIG. 8(B) is a side view of the inflation portion when viewed in the direction along the wearing surface.

FIG. 9(A) is a front view of the inflation portion when viewed from the wearing surface side, and FIG. 9(B) is a side view of the inflation portion when viewed in the direction along the wearing surface.

FIG. 10(A) is a front view of the inflation portion when viewed from the wearing surface side, and FIG. 10(B) is a side view of the inflation portion when viewed in the direction along the wearing surface.

FIG. 11(A) is a front view of the inflation portion when viewed from the wearing surface side, and FIG. 11(B) is a side view of the inflation portion when viewed in the direction along the wearing surface.

FIG. 12(A) is a front view of the inflation portion when viewed from the wearing surface side, and FIG. 12(B) is a side view of the inflation portion when viewed in the direction along the wearing surface.

FIG. 13(A) is a front view of the inflation portion when viewed from the wearing surface side, and FIG. 13(B) is a side view of the inflation portion when viewed in the direction along the wearing surface.

FIG. 14(A) is a front view of the inflation portion when viewed from the wearing surface side, and FIG. 14(B) is a side view of the inflation portion when viewed in the direction along the wearing surface.

DESCRIPTION OF EMBODIMENTS

Figure 1:
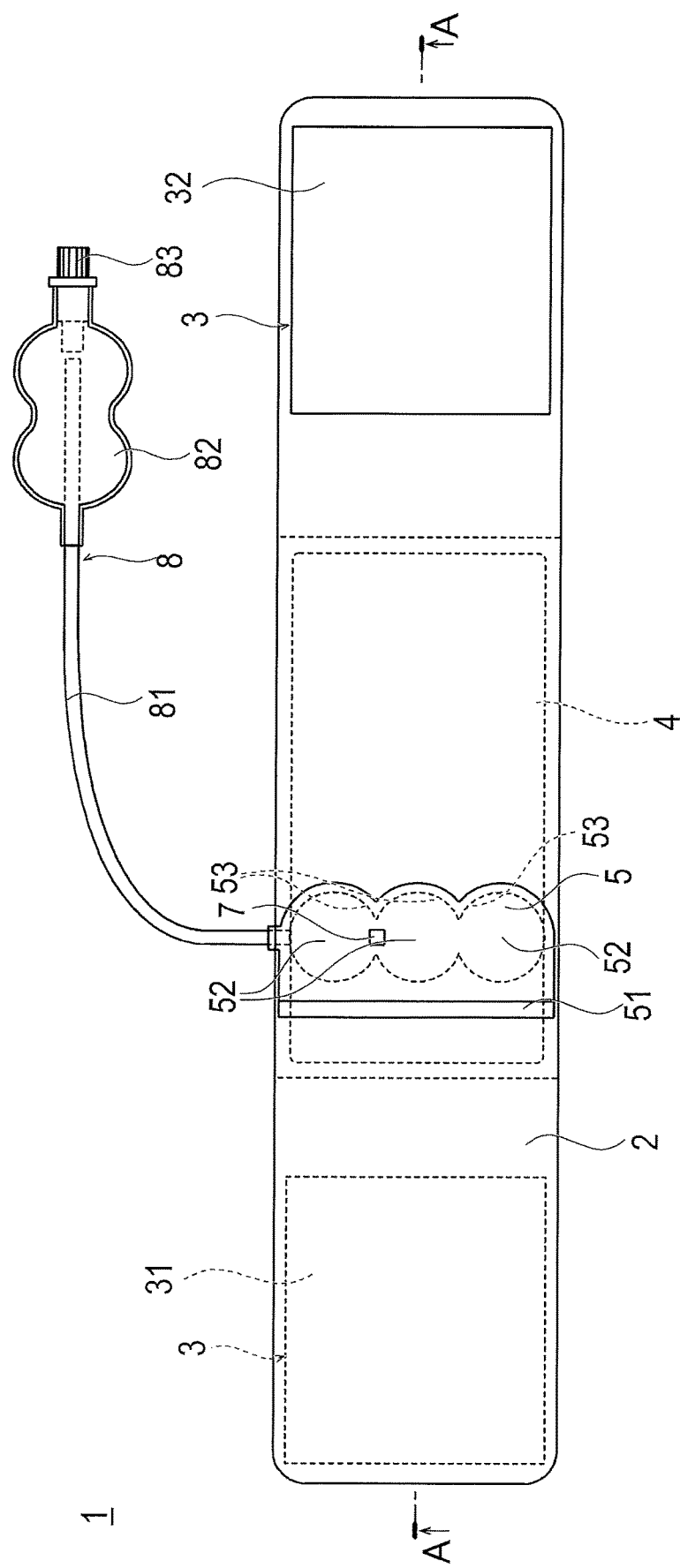
FIG. 1 is a plan view of a hemostatic device according to an exemplary embodiment of the disclosure when viewed from a wearing surface side.

Hereinafter, an exemplary embodiment according to the disclosure herein will be described with reference to the drawings. Note that, dimensional proportions in the drawings may be exaggerated and different from actual proportions for convenience of description in some cases.

Figure 2:
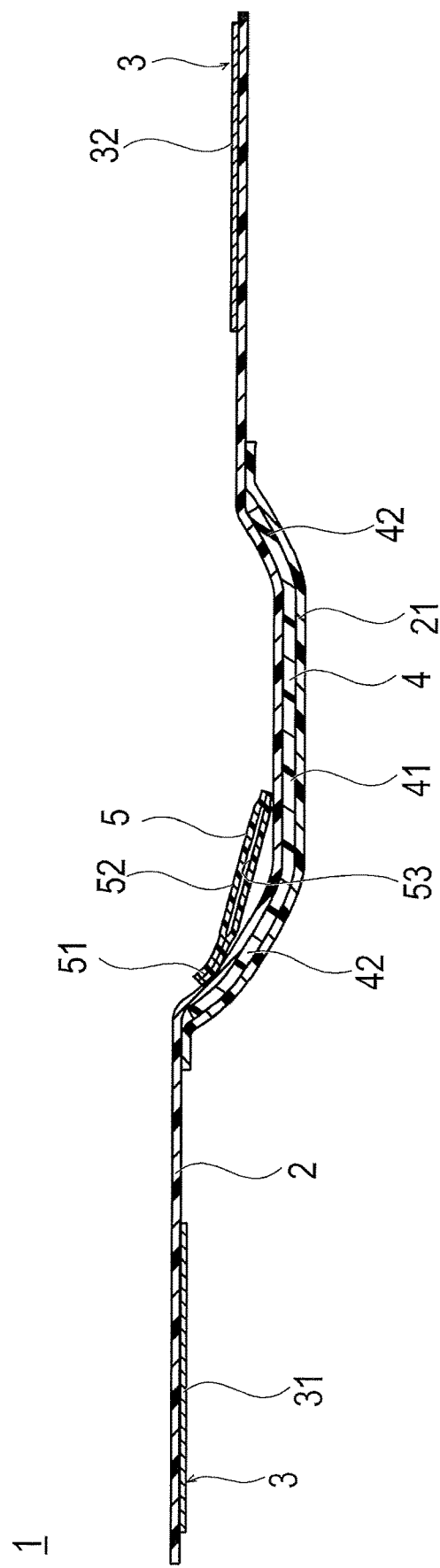
FIG. 2 is a cross-sectional view taken along line A-A in FIG. 1.
Figure 3:
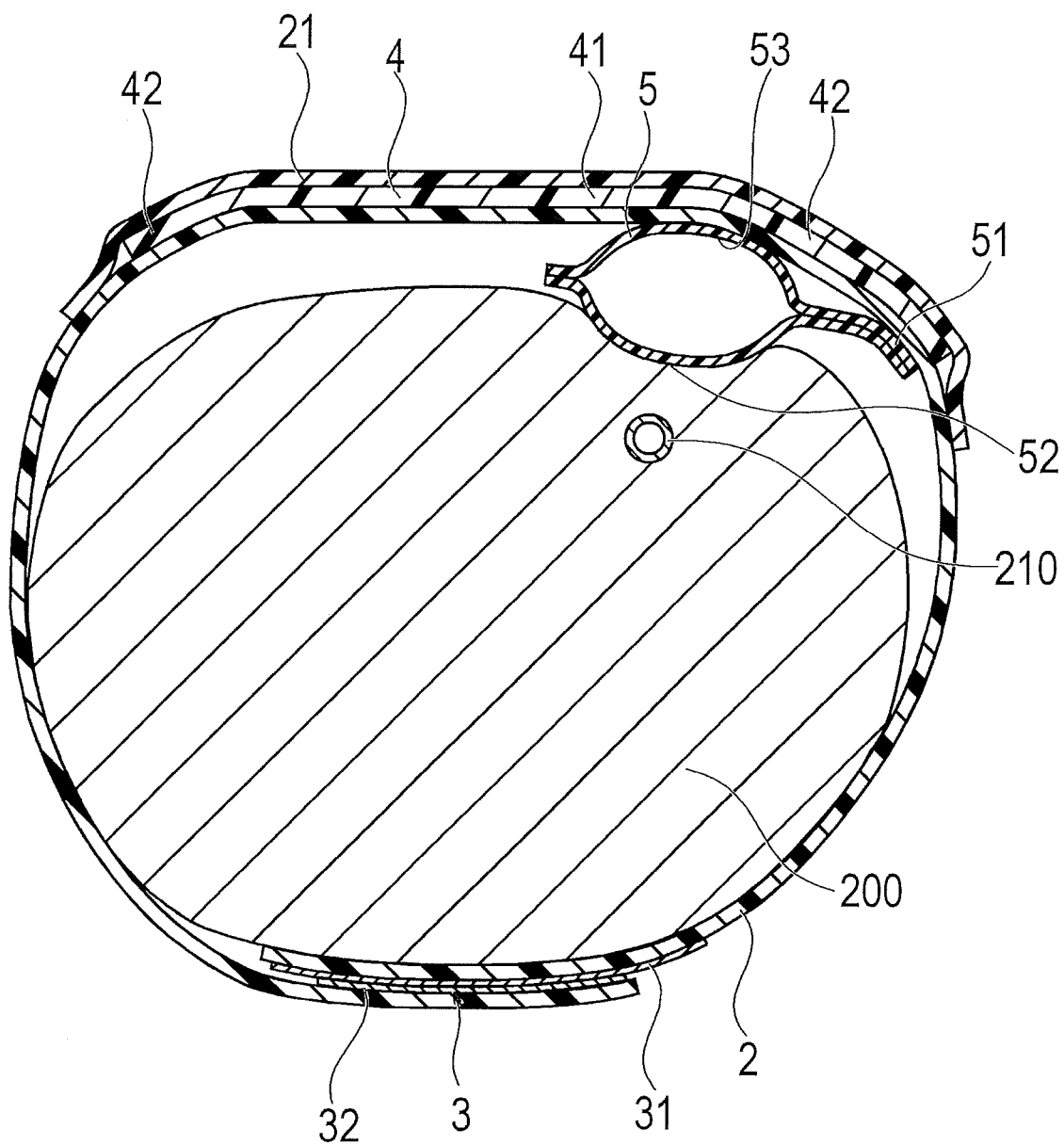
FIG. 3 is a lateral sectional view illustrating a state where a user wears the hemostatic device according to the exemplary embodiment.
Figure 4:
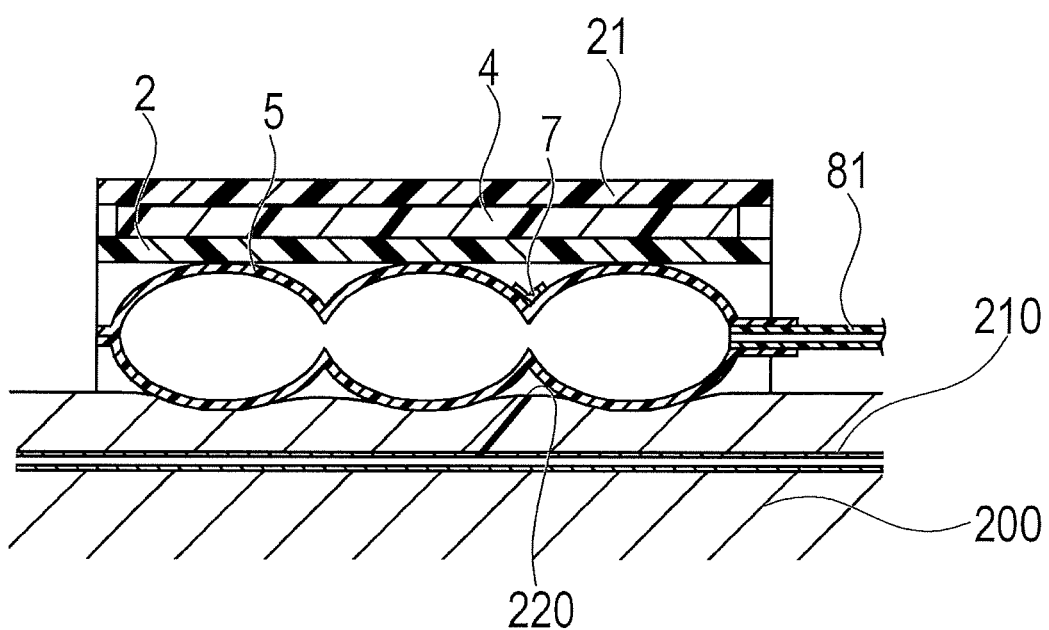
FIG. 4 is a longitudinal sectional view illustrating a state where a user wears the hemostatic device according to the exemplary embodiment.
Figure 5:
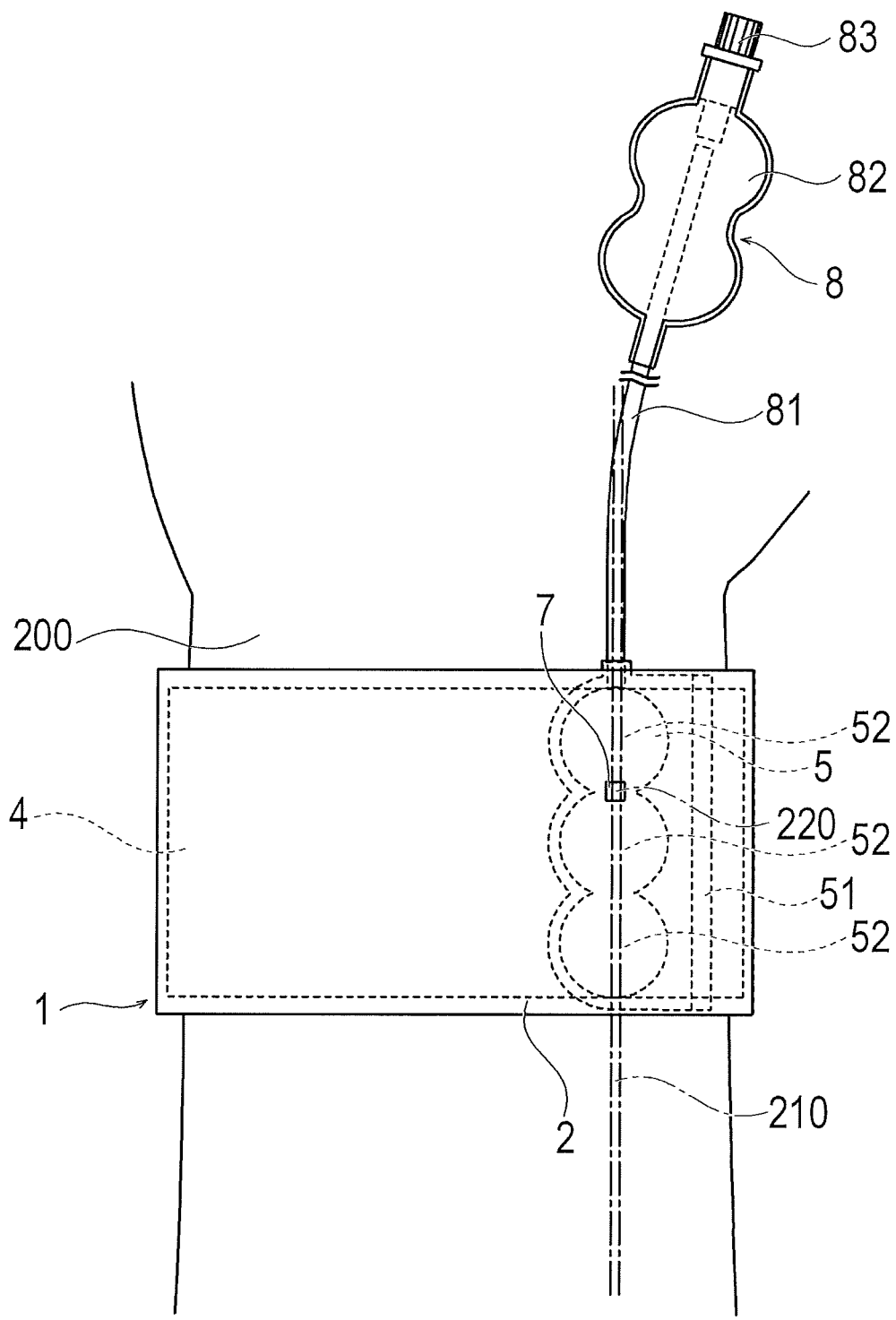
FIG. 5 is a plan view illustrating a state where a user wears the hemostatic device according to the exemplary embodiment.

A hemostatic device 1 according to an exemplary embodiment of the disclosure is used as follows. As illustrated in FIGS. 3 and 4, in order to insert a catheter for treatment and inspection into a blood vessel, an introducer sheath is caused to indwell a puncture site 220 (hemostasis-requiring site) formed in a radial artery 210 of a wrist 200 (limb), and is removed therefrom. Thereafter, the hemostatic device 1 is used for performing hemostasis at the puncture site 220. As illustrated in FIGS. 1 and 2, the hemostatic device 1 includes a band 2 for being wrapped around the wrist 200, a surface fastener 3 (securing portion) that secures the band 2 in a state where the band 2 is wrapped around the wrist 200, a curved plate 4, an inflation portion 5, a marker 7, and an injector 8.

The band 2 is a flexible band-like member. The band 2 is wrapped substantially once around an outer periphery of the wrist 200. A curved plate holder 21 for holding the curved plate 4 is formed in a central portion of the band 2. The curved plate holder 21 is adapted to have double layer construction in such a way that a separate band-like member is joined to the outer surface side (or the inner surface side) by means of welding (heat-welding, high frequency welding, or ultrasound welding) or adhesion (adhesion using an adhesive or a solvent), thereby holding the curved plate 4 inserted into a gap between the double layer structure.

A male side (or a female side) 31 of the surface fastener 3, such as a hook and loop fastener (e.g., a product commonly known as VELCRO® or Magic Tape in Japan) is installed on an outer surface side of a portion of the band 2, in the vicinity of the left end in FIG. 1. A female side (or a male side) 32 of the surface fastener 3 is installed on an inner surface side of a portion of the band 2, in the vicinity of the right end in FIG. 1. The band 2 is wrapped around the wrist, and the male side 31 and the female side 32 are joined to each other, thereby allowing a user to wear the band 2 on the wrist 200. Note that, without being limited to the surface fastener 3, means for securing the band 2 in a state where the band 2 is wrapped around the wrist 200 may be a snap, a button, a clip, or a frame member passing through the end portion of the band 2, for example.

A material of the band 2 is not particularly limited as long as the material is flexible. For example, the material may include polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyimide elastomer, polyurethane elastomer, and polyester elastomer, or any optional combination thereof (blend resin, polymer alloy, and laminate).

In addition, it is preferable that the band 2 is substantially transparent. In this manner, the puncture site 220 is reliably visible from the outside, and the marker 7 (to be described later) can be easily aligned with the puncture site 220.

The curved plate (hard plate) 4 is held in the band 2 by being inserted between the double layer structure formed in the curved plate holder 21 of the band 2. At least a portion of the curved plate 4 has a shape which is curved toward the inner surface side (wearing surface side). The curved plate 4 is configured to include a material harder than that of the band 2, and is designed to maintain a substantially constant shape.

The curved plate 4 has a long shape in the longitudinal direction of the band 2. The central portion 41 in the longitudinal direction of the curved plate 4 has a flat plate shape having almost no curved portion, and both sides of the central portion 41 respectively have curved portions 42 which are curved toward the inner peripheral side and along the longitudinal direction (circumferential direction of the wrist 200) of the band 2.

A configuration material of the curved plate 4 is not particularly limited as long as the puncture site 220 is visible through the material. For example, polyolefin such as acrylic resin, polyvinyl chloride (particularly rigid polyvinyl chloride), polyethylene, polypropylene, and polybutadiene, polyester such as polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), and polybutylene terephthalate (PBT), butadiene-styrene copolymer, fluorine resin such as aromatic or aliphatic polyamide, and polytetrafluoroethylene are exemplified.

When the curved plate 4 is substantially transparent, the puncture site 220 is reliably visible from the outside, and the marker 7 (to be described later) can be easily aligned with the puncture site 220.

Note that, the curved plate 4 may not have a portion which is not curved as in the flat plate shape of central portion 41, that is, the curved plate 4 may be curved over the full length.

The inflation portion 5 is configured to include a flexible material that interlocks with the band 2. The inflation portion 5 inflates when a fluid (a gas such as air or a liquid) is injected, and compresses the puncture site 220 of the wrist 200.

The inflation portion 5 is located so as to eccentrically overlap one end side in the longitudinal direction of the curved plate 4 held in the band 2. That is, in the illustrated configuration, the inflation portion 5 is located so as to overlap the vicinity between the curved portion 42 on the left end side of the curved plate 4 in FIG. 2 and the central portion 41.

Note that, in a case where the inflation portion 5 is located so as to eccentrically overlap one end side of the curved plate 4 in the longitudinal direction, in the curved portions 42 located on both sides of the curved plate 4, the curved portion 42 on the side where the inflation portion 5 is located (one end side of the curved plate 4) is longer in the longitudinal direction. In this manner, when a user wears the hemostatic device 1 on the wrist 200 and inflates the inflation portion 5, the curved portion 42 on the other end side of the curved plate 4 comes into contact with the wrist. Accordingly, it is possible to reduce the risk of pain occurrence.

A configuration material of the inflation portion 5 is not particularly limited as long as the puncture site 220 is visible through the material. For example, the same material as the configuration material of the above-described band 2 can be used. In addition, it is preferable that the inflation portion 5 is configured to include a material the same as or similar to the material of the band 2. In this manner, the inflation portion 5 can be easily joined to the band 2 by means of welding, and can be easily manufactured.

It is preferable that the inflation portion 5 is substantially transparent. In this manner, the puncture site 220 is reliably visible from the outside, and the marker 7 (to be described later) can be easily aligned with the puncture site 220.

For example, a structure of the inflation portion 5 can be formed in a bag shape in which two sheet materials formed of the above-described materials overlap each other and edge portions thereof are joined to each other by using a welding method or an adhesion method.

The inflation portion 5 is formed in such a way that the plurality (three in the present embodiment) of convex portions 52 which have a convex shape to the wearing surface side (inner surface side when worn on the wrist) when the inflation portion 5 inflates by the injected fluid are aligned with each other in the width direction orthogonal to the longitudinal direction of the band 2. The inflation portion 5 has three unitary spaces 53 internally which have a circular shape when viewed from the wearing surface side, and which overlap and communicate with each other in the width direction. Note that, the convex portion 52 may have the convex shape or may not have the convex shape in a state before the inflation portion 5 inflates.

The inflation portion 5 formed in this way interlocks with the band 2 via a flexible holder 51. Note that, it is preferable that the holder 51 is configured to include the same material as that of the inflation portion 5.

The marker 7 is disposed on the outer surface side of the inflation portion 5, that is, a side not in contact with the puncture site 220. This marker 7 is disposed in the inflation portion 5, thereby enabling the inflation portion 5 to be easily aligned with the puncture site 220. Blood leakage or hematoma is thus restrained from occurring due to misalignment of the inflation portion 5.

The marker 7 is located on a side with which the injector 82 of the inflation portion 5 interlocks in the width direction of the band 2. In addition, the marker 7 is disposed between two adjacent convex portions 52 of the inflation portion 5. That is, it is preferable that the marker 7 is eccentrically disposed on one side in the width direction of the band 2.

As best shown in FIG. 4, the marker 7 is preferably disposed between the two adjacent convex portions 52 of the inflation portion 5. Hence, when properly sighted, the convex portions 52 of the inflation portion 5 barely apply the compressive force directly to the puncture site 220 existing on the outer surface (skin) of the limb, but rather, the compressive force can be applied to the puncture site of the blood vessel (refer to FIG. 4). In addition, in a case where the limb is punctured and the introducer sheath indwells the limb, the introducer sheath indwells by puncturing the limb at an angle of 30° to 45° with respect to the outer surface (skin) of the limb. Accordingly, the puncture site 220 present in the skin is different from the puncture site present in the blood vessel. Therefore, even if the hemostatic device 1 does not apply the compressive force from the convex portion 52 directly to the puncture site 220 present on the outer surface (skin) of the limb, the hemostatic device 1 can apply the compressive force from the convex portion 52 to only the puncture site of the blood vessel. Therefore, the hemostatic device 1 can sufficiently perform hemostasis at the puncture site while relieving pain caused by the inflation portion 5.

A shape of the marker 7 is not particularly limited. For example, circular, triangular, and quadrangular shapes may be employed. The present exemplary embodiment employs the quadrangular shape.

A size of the marker 7 is not particularly limited. However, for example, in a case where the shape of the marker 7 is quadrangular, it is preferable that the length of one side of the marker 7 is in a range of 1 to 4 mm. If the length of one side is 5 mm or longer, the size of the marker 7 becomes larger than the size of the puncture site 220. Consequently, the central portion of the inflation portion 5 is less likely to be aligned with the puncture site 220.

A material of the marker 7 is not particularly limited. For example, oil coloring agents such as ink or resins kneaded with pigments may be employed.

A color of the marker 7 is not particularly limited as long as the inflation portion 5 can be aligned with the puncture site 220 through the color. However, it is preferable to employ a green-based color. If the green-based color is employed, the marker 7 is easily visible on the blood or the skin. Accordingly, the inflation portion 5 can be more easily aligned with the puncture site 220.

In addition, it is preferable that the marker 7 is translucent. In this manner, the puncture site 220 is visible from the outside of the marker 7.

A method of disposing the marker 7 in the inflation portion 5 is not particularly limited. For example, a method of printing the marker 7 on the inflation portion 5, a method of welding the marker 7 to the inflation portion 5, or a method of applying an adhesive to one surface of the marker 7 so as to adhere to the inflation portion 5 may be employed.

Note that, the marker 7 may be disposed on the inner surface side of the inflation portion 5, that is, a surface of the inflation portion 5 which faces towards and comes into contact with the puncture site 220. In this case, it is preferable that the marker 7 is disposed on the inner surface inside the inflation portion 5 so as not to come into direct contact with the puncture site 220.

Alternatively, the marker 7 may not be disposed in the inflation portion 5, but instead, the marker 7 may be disposed in the band 2 or the curved plate 4. Even in this case, it is preferable that the marker 7 is disposed so as to be located between the adjacent convex portions 52.

The injector 8 is a portion for injecting the fluid into the inflation portion 5, and is connected to the inflation portion 5 as illustrated in FIG. 1. The injector 8 is configured to include a flexible tube 81 whose proximal portion is connected to the inflation portion 5 and whose lumen communicates with the inside of the inflation portion 5, a bag body 82 installed in the distal portion of the tube 81 so as to communicate with the lumen of the tube 81, and a tubular connector 83 connected to the bag body 82. A check valve (not illustrated) is incorporated in the connector 83.

In order for the inflation portion 5 to be inflated (expanded), a distal tubular portion of a syringe (not illustrated) is inserted into the connector 83, and the check valve is opened. A plunger of the syringe is pushed, and a fluid contained inside the syringe is injected into the inflation portion 5 via the injector 8. If the inflation portion 5 expands, the bag body 82 communicating with the inflation portion 5 via the tube 81 also expands, a user can visually confirm that the inflation portion 5 is pressurized without the fluid leaking. After the fluid is injected into the inflation portion 5, if the distal tubular portion of the syringe is removed from the connector 83, the check valve incorporated in the connector 83 is closed. In this manner, leakage of the fluid is prevented, thereby maintaining a state where the inflation portion 5 is expanded.

Next, a method of using the hemostatic device 1 according to the exemplary embodiment will be described.

Before a user wears the hemostatic device 1 on the wrist 200, the inflation portion 5 is not in an inflated state. In a case where the wrist 200 is punctured, normally, the puncture site 220 on the radial artery 210 is eccentrically located on the thumb side on the inner side (side having a tendon) of the wrist 200 of the right hand. Normally, the introducer sheath indwells the puncture site 220. The band 2 is wrapped around the wrist 200 while maintaining a state where the introducer sheath indwells the puncture site 220. The inflation portion 5 and the band 2 are aligned so that the marker 7 disposed in the inflation portion 5 overlaps the puncture site 220. The male side 31 and the female side 32 of the surface fastener 3 are brought into contact with and joined to each other, thereby enabling the user to wear the band 2 on the wrist 200. The hemostatic device 1 is worn on the wrist 200 so that the injector 8 interlocking with the inflation portion 5 faces the downstream side of the blood flow of the radial artery 210. In this manner, the injector 8 can be operated without interfering with a procedure on the upstream side from the wrist or an instrument (for example, a blood pressure gauge) located on the upstream side. In addition, the hemostatic device 1 is worn on the right wrist 200 so that the injector 8 faces the downstream side. Accordingly, the inflation portion 5 disposed so as to eccentrically overlap one side of the curved plate 4 is aligned and located along the radial artery 210 eccentrically located on the thumb side on the inner side of the wrist 200. The plurality of convex portions 52 of the inflation portion 5 are also aligned with each other along the width direction of the band 2 and thus, the convex portions 52 are aligned with each other along the radial artery 210. The marker 7 is disposed between the two convex portions 52 on the side opposite to the side with which the injector 8 of the inflation portion 5 interlocks. Accordingly, if the marker 7 is aligned with the puncture site 220, two convex portions 52 are located on the upstream side from the puncture site 220 of the radial artery 210, and one convex portion 52 is located on the downstream side from the puncture site 220.

After the hemostatic device 1 is worn on the wrist 200, the syringe (not illustrated) is connected to the connector 83 of the injector 8, and fluid is injected into the inflation portion 5 as described above. As illustrated in FIGS. 3 and 4, the inflation portion 5 is caused to inflate. Depending on the specifics of a medical case, the degree of inflation of the inflation portion 5, that is, the compressive force applied to the puncture site 220 can be easily adjusted by determining the amount of injection fluid. Therefore, operability of the hemostatic device 1 is improved.

After the inflation portion 5 is caused to inflate, the syringe is detached from the connector 83. Then, the introducer sheath is removed from the puncture site 220. In this manner, the inflation portion 5 maintains an inflated state, thereby maintaining a state where the inflation portion 5 compresses the puncture site 220.

When the inflation portion 5 inflates, three convex portions 52 aligned with each other along the radial artery 210 press the body surface of the wrist 200. The upstream side from the puncture site 220 of the radial artery 210 is compressed by two convex portions 52, and the downstream side from the puncture site 220 is compressed by one convex portion 52. In this case, a site overlapping the puncture site 220 of the inflation portion 5 is not in contact with the puncture site 220 on the skin side. Alternatively, even if the site is in contact with the puncture site 220, the compressive force is small. In this manner, the hemostatic device 1 according to the disclosure herein can reduce the possibility that the inflation portion 5 may directly compress the puncture site 220 on the skin side. Accordingly, it is possible to minimize an excessive stress on a puncture wound, and it is possible to reduce factors that a patient is likely to feel pain. In addition, the hemostatic device 1 according to the disclosure herein does not locally compress the puncture site 220, and can perform the hemostasis at the puncture site 220 while applying the dispersed compressive force to the plurality of locations along the blood vessel at a plurality of places. Therefore, the hemostatic device 1 suppresses the occurrence of pain in a patient. Furthermore, the hemostatic device 1 according to the disclosure compresses the upstream side of the blood vessel and the downstream side of the blood vessel by causing the convex portions 52 to pinch the puncture site 220. Accordingly, it is possible to achieve an excellent hemostatic effect. Note that, the site overlapping the puncture site 220 of the inflation portion 5 is not in direct contact with the puncture site 220. However, the periphery of the puncture site 220 is compressed so as to apply the compressive force into the body. Accordingly, it is possible to inhibit bleeding from the puncture site 220.

In addition, the puncture site 220 on the skin side is disposed between the convex portions 52. Accordingly, an excessive stress is not put on a wound, and thus, pain can be relieved.

If one location of the blood vessel is compressed, blood flows are greatly different between the pressurized site and the site not pressurized. When decompressed, there is a possibility that a blood crust (scab) which can be generated at the puncture site may be easily broken off by the blood flow. The hemostatic device 1 according to the disclosure herein compresses the blood vessel at the plurality of locations. Therefore, when decompressed, it is possible to more reliably prevent the scab from being broken off.

In addition, the plurality of locations are compressed along the blood flow by the plurality of convex portions 52. Accordingly, the blood flow stays at the plurality of locations. Therefore, it is possible to create an environment where platelets are likely to coagulate at the puncture site 220.

The hemostatic device 1 causes two convex portions 52 to compress the upstream side from the puncture site 220 of the radial artery 210, and causes one convex portion 52 to compress the downstream side from the puncture site 220 of the radial artery 210. Therefore, in the hemostatic device 1, the compressive force applied to the upstream side from the puncture site 220 of the radial artery 210 is stronger than the compressive force applied to the downstream side in the radial artery 210. Therefore, in the hemostatic device 1, the compressive force applied to the upstream side of the blood vessel, which is closer to the heart and has higher blood pressure, can be stronger than the compressive force applied to the downstream side of the blood vessel. In this manner, in accordance with the blood pressure, the compressive force applied by the inflation portion 5 can be distributed in a well-balanced manner. Therefore, it is possible to achieve an excellent hemostatic effect while stress on a living body is reduced as much as possible without excessively restricting a blood flow.

When the inflation portion 5 inflates, the curved plate 4 is separated from the body surface of the wrist 200, and becomes less likely to come into contact with the wrist 200. In addition, when the hemostatic device 1 causes the inflation portion 5 to inflate after a user wears the hemostatic device 1, the curved plate 4 restrains the inflation portion 5 from inflating in a direction away from the body surface of the limb. Accordingly, the compressive force of the inflation portion 5 concentrates on the hemostasis-requiring blood vessel. In this manner, the compressive force applied from the inflation portion 5 concentrates on the periphery of the puncture site 220. Accordingly, a hemostatic effect is improved, and it is possible to avoid a possibility of compressing other blood vessels or nerves which do not require the hemostasis. Therefore, it is possible to effectively prevent the occurrence of hand numbness or poor blood circulation.

When the hemostatic device 1 is removed, the syringe is connected to the connector 83 of the injector 8, the fluid contained in the inflation portion 5 is aspirated using the syringe, and the fluid is discharged, thereby deflating the inflation portion 5. Thereafter, if the male side 31 and the female side 32 of the surface fastener 3 are detached from each other, the hemostatic device 1 can be removed from the wrist 200. Note that, when the hemostatic device 1 is removed, the inflation portion 5 may not have to deflate.

Note that, in the hemostatic device 1, before the hemostatic device 1 is removed, an operation for decompressing the inflation portion 5 may be performed with the lapse of time in order to adjust the pressure applied by the inflation portion 5 to the vicinity of the puncture site 220.

As described above, the hemostatic device 1 according to the disclosure has the flexible band 2 that can be wrapped around the hemostasis-requiring site of the limb, the surface fastener 3 (the securing portion) that secures the band in a state where the band is wrapped around the limb, and the inflation portion 5 that interlocks with the band 2, and that inflates when the fluid is injected. The inflation portion 5 has the plurality of convex portions 52 which are aligned with each other in the width direction orthogonal to the longitudinal direction of the band 2 when the inflation portion inflates. In this manner, when the band 2 is wrapped around the limb, the convex portions 52 are arranged while being aligned with each other along the direction in which the radial artery 210 for the hemostasis extends. Therefore, the plurality of convex portions 52 can apply the dispersed compressive force to the plurality of locations along the blood vessel. Accordingly, the hemostasis can be performed while pain occurrence is suppressed as much as possible. Note that, the length of the band 2 in the longitudinal direction is longer than the length of the band 2 in the width direction. Accordingly, the band 2 can be sufficiently wrapped around the limb such as the wrist.

Furthermore, the convex portions 52 are disposed on both the upstream side of the blood vessel and the downstream side of the blood vessel by pinching the puncture site 220 of the blood vessel. While the dispersed compressive force is applied by the convex portions 52, the hemostasis can be performed at the puncture site 220 from the periphery of the puncture site 220. Accordingly, the hemostasis can be performed while pain occurrence is suppressed as much as possible. In addition, the puncture site 220 is disposed between the convex portions 52. Accordingly, an excessive stress is not put on a wound, and thus, pain can be relieved.

In addition, the hemostatic device 1 has the marker 7 for aligning the inflation portion 5 with the puncture site 220. In this manner, the hemostatic device 1 aligns the marker 7 with the puncture site 220. Accordingly, the hemostatic device 1 can cause the inflation portion 5 to compress a desired position of the body surface. Therefore, the hemostatic device 1 can restrain blood leakage caused by misalignment of the inflation portion 5, and can reliably perform the hemostasis at the puncture site 220.

In addition, the marker 7 is disposed between two adjacent convex portions 52. Thus, the hemostatic device aligns the marker 7 with the puncture site 220. Accordingly, when the inflation portion 5 inflates, the puncture site 220 can be pinched between the two convex portions 52. Therefore, the hemostatic device 1 can pinch and compress both the upstream side and the downstream side of the puncture site 220 of the blood vessel. Accordingly, the hemostatic device 1 can restrain the convex portions 52 from excessively compressing the puncture site 220. In this manner, the hemostatic device 1 can achieve an excellent hemostatic effect while relieving pain.

In addition, the marker 7 is eccentrically disposed on one side in the width direction of the band 2. In this manner, the hemostatic device 1 aligns the marker 7 with the puncture site 220. Accordingly, when the inflation portion 5 is disposed at the puncture site 220, it becomes easier to set the compressive force applied to the upstream side of the blood vessel by the inflation portion 5 to be stronger than the compressive force applied to the downstream side of the blood vessel. Therefore, the compressive force applied to the upstream side of the blood vessel, which is closer to the heart and has higher blood pressure, can be stronger than the compressive force applied to the downstream side of the blood vessel. Accordingly, it is possible to achieve an excellent hemostatic effect while strain on a living body is reduced as much as possible without excessively inhibiting a blood flow.

In addition, the hemostatic device 1 may have the curved plate 4 formed of a material harder than that of the band 2. The band 2 may be configured to hold the curved plate 4 so as to overlap the inflation portion 5. In this manner, if the hemostatic device 1 causes the inflation portion 5 to inflate after a user wears the hemostatic device 1, the curved plate 4 restrains the inflation portion 5 from inflating in a direction away from the body surface of the limb. Accordingly, the compressive force of the inflation portion 5 concentrates on the hemostasis-requiring blood vessel. Therefore, a hemostatic effect is improved, and it is possible to avoid a possibility of compressing other blood vessels or nerves which do not require the hemostasis. Accordingly, it is possible to reduce the occurrence of hand numbness or poor blood circulation. In addition, the curved plate 4 is curved. Accordingly, the compressive force of the inflation portion 5 can be effectively received by the curved plate 4. An excellent hemostatic effect can be achieved by effectively adjusting the compressive force to be applied to the limb.

Note that, the disclosure herein is not limited to only the above-described embodiment, and can be modified in various ways by those skilled in the art within the technical concept of the disclosure. For example, each portion configuring the hemostatic device can be substituted with any optional configuration which can fulfill the same function. In addition, any optional configuration may be added thereto.

The hemostatic device according to the disclosure herein is not limited to those which are used by being wrapped around the wrist. The disclosure is also applicable to the hemostatic device which is used by being wrapped around any site of an arm or a leg (collectively, referred to as the "limb" in this specification).

Figure 6A:
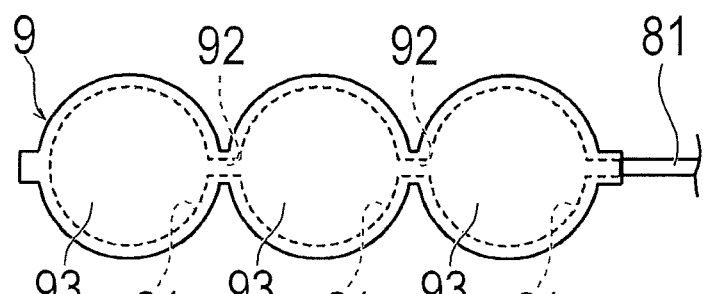
FIGS. 6(A) and 6(B) illustrate a first modified example of an inflation portion.
Figure 6B:
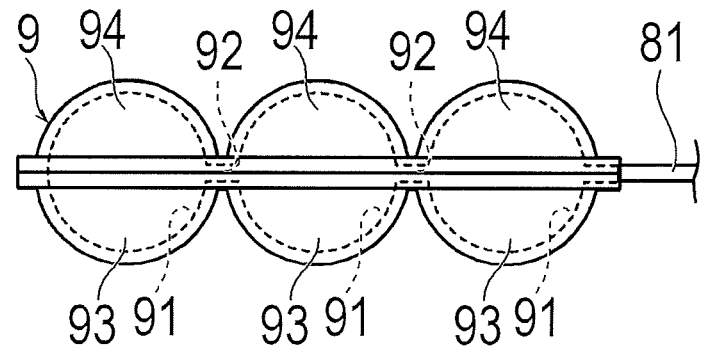

In addition, a configuration of the inflation portion is not limited to the above-described embodiment. For example, in an inflation portion 9 according to a first modified example illustrated in FIGS. 6(A) and 6(B), unitary spaces 91 which are circular when viewed from the wearing surface side may be formed so as to communicate with each other through a communicating section 92. When the inflation portion 9 inflates, the inflation portion 9 has a hemispherical convex portion 93 on the wearing surface side, and has a hemispherical support portion 94 which protrudes symmetrically with the convex portion 93, on the side opposite to the wearing surface side. The support portion 94 supports the convex portion 93 by coming into contact with the band 2, and performs a role of efficiently applying the compressive force to the blood vessel, thereby improving a hemostatic effect.

Figure 7A:
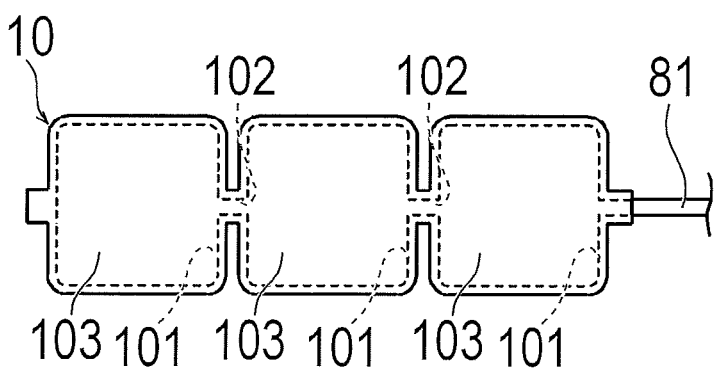
FIGS. 7(A) and 7(B) illustrate a second modified example of an inflation portion.
Figure 7B:
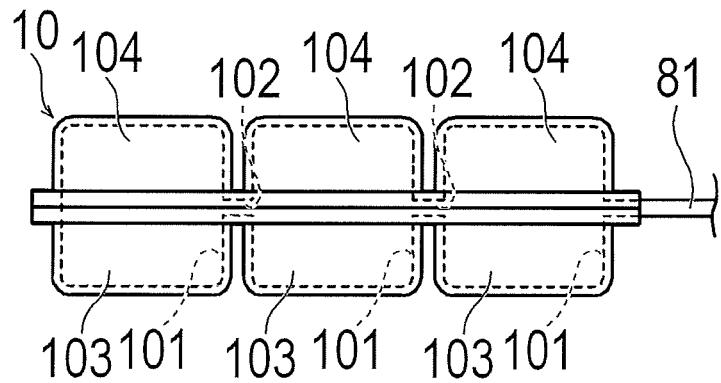

In addition, in an inflation portion 10 according to a second modified example illustrated in FIGS. 7(A) and 7(B), unitary spaces 101 which are substantially rectangular when viewed from the wearing surface side may be formed so as to communicate with each other through a communicating section 102. When the inflation portion 10 inflates, the inflation portion 10 has a convex portion 103 which is substantially prismatic on the wearing surface side, and has a support portion 104 which is substantially prismatic and protrudes symmetrically with the convex portion 103 on the side opposite to the wearing surface side. The support portion 104 supports the convex portion 103 by coming into contact with the band 2, and performs a role of efficiently applying the compressive force to the blood vessel, thereby improving a hemostatic effect.

Figure 8A:
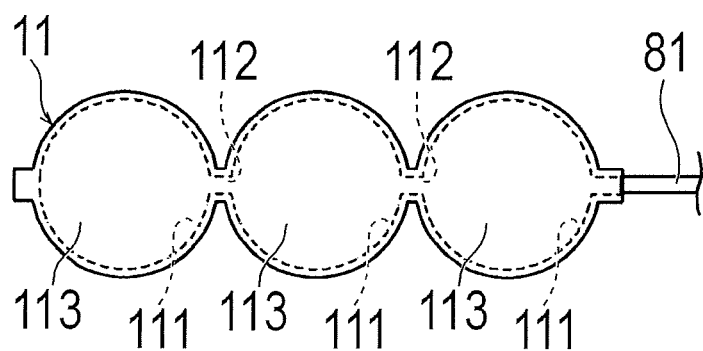
FIGS. 8(A) and 8(B) illustrate a third modified example of an inflation portion.
Figure 8B:
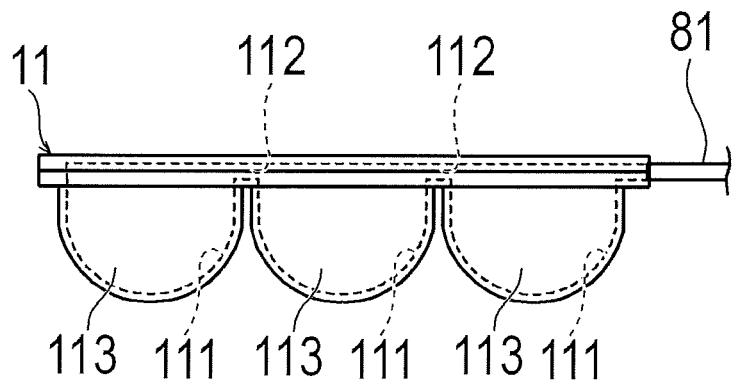

Further, in an inflation portion 11 according to a third modified example illustrated in FIGS. 8(A) and 8(B), unitary spaces 111 which are substantially circular when viewed from the wearing surface side may be formed so as to communicate with each other through a communicating section 112. When the inflation portion 11 inflates, the inflation portion 11 has a convex portion 113 formed in a shape in which a hemisphere is coupled with an apex of the column on the wearing surface side, and the side opposite to the wearing surface side is formed flat. The convex portion 113 is formed long in a protruding direction by coupling the hemisphere with the column. Therefore, each convex portion 113 is likely to locally come into contact with a target site on the body surface. Therefore, it is possible to improve a hemostatic effect by applying a proper compressive force without excessively dispersing the compressive force. Note that, the fluid is injected into the inflation portion 11 so that the convex portion 113 protrudes toward the wearing surface side, and the side opposite to the wearing surface becomes flat. For example, the above-described configuration can be realized as follows. Two overlapping sheet materials are shaped in advance, or mutually different materials are used for the two overlapping sheet materials. Alternatively, mutually different thicknesses are employed for the two overlapping sheet materials.

Figure 9A:
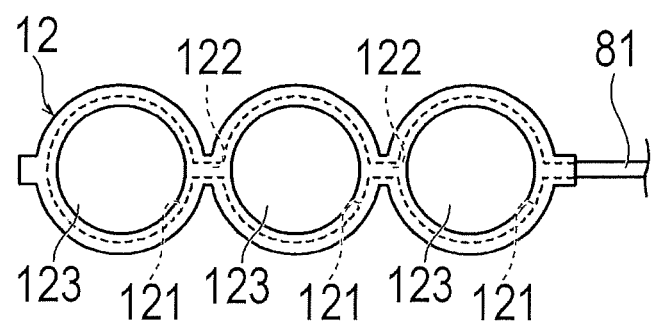
FIGS. 9(A) and 9(B) illustrate a fourth modified example of an inflation portion.
Figure 9B:
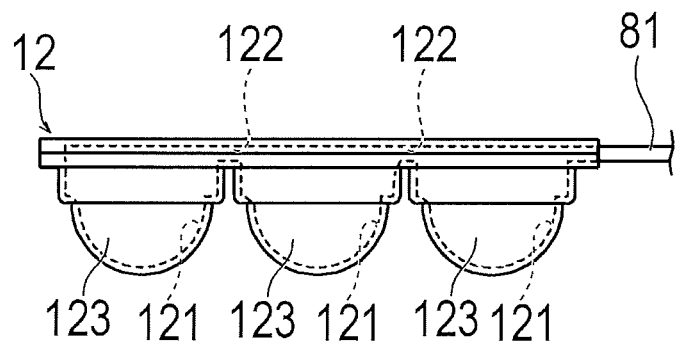

In addition, in an inflation portion 12 according to a fourth modified example illustrated in FIGS. 9(A) and 9(B), unitary spaces 121 which are circular when viewed from the wearing surface side may be formed so as to communicate with each other through a communicating section 122. When the inflation portion 12 inflates, the inflation portion 12 has a convex portion 123 formed in a shape with which a hemisphere having a diameter smaller than the diameter of the column is coupled, on the wearing surface side. In addition, when the inflation portion 12 inflates, the side opposite to the wearing surface side is formed flat. The convex portion 123 is formed long in the protruding direction by coupling the hemisphere having a diameter smaller than the diameter of the column with the column. Therefore, each convex portion 123 is likely to locally come into contact with the target site on the body surface. Therefore, the inflation portion 12 can improve a hemostatic effect by applying a proper compressive force without excessively dispersing the compressive force.

Figures 10A, 10B:
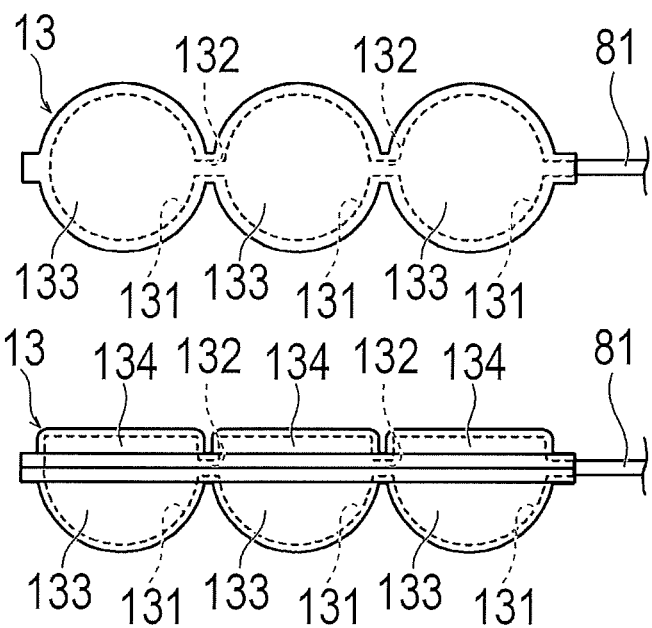
FIGS. 10(A) and 10(B) illustrate a fifth modified example of an inflation portion.

In addition, in an inflation portion 13 according to a fifth modified example illustrated in FIGS. 10(A) and 10(B), unitary spaces 131 which are circular when viewed from the wearing surface side may be formed so as to communicate with each other through a communicating section 132. When the inflation portion 13 inflates, the inflation portion 13 has a hemispherical convex portion 133 on the wearing surface side, and has a support portion 134 which protrudes in a column shape, on the side opposite to the wearing surface side. The support portion 134 supports the convex portion 133 by coming into contact with the band 2, and performs a role of efficiently applying the compressive force to the blood vessel, thereby improving a hemostatic effect.

Figures 11A, 11B:
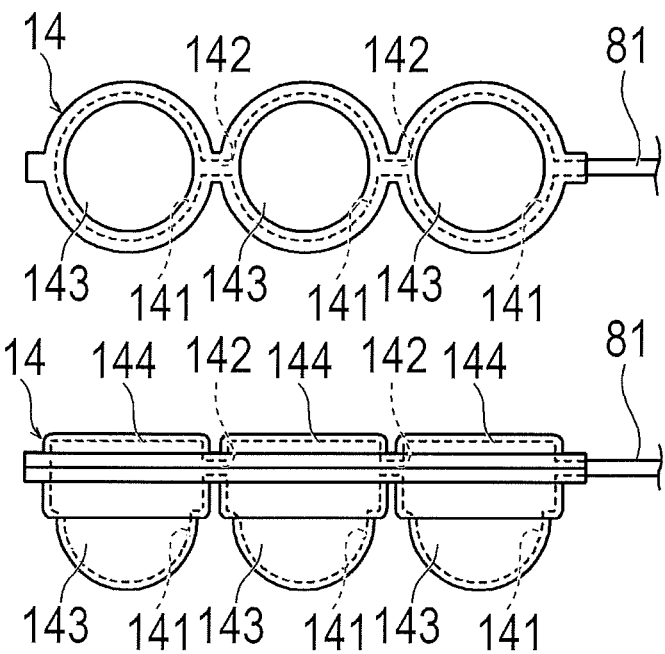
FIGS. 11(A) and 11(B) illustrate a sixth modified example of an inflation portion.

In addition, in an inflation portion 14 according to a sixth modified example illustrated in FIGS. 11(A) and 11(B), unitary spaces 141 which are circular when viewed from the wearing surface side may be formed so as to communicate with each other through a communicating section 142. When the inflation portion 14 inflates, the inflation portion 14 has a convex portion 143 formed in a shape with which a hemisphere having a diameter smaller than the diameter of the column is coupled with an apex of the column, on the wearing surface side. In addition, when the inflation portion 14 inflates, the inflation portion 14 has a support portion 144 which protrudes in a column shape, on the side opposite to the wearing surface side. The support portion 144 supports the convex portion 143 by coming into contact with the band 2, and performs a role of efficiently applying the compressive force to the blood vessel, thereby improving a hemostatic effect.

Figure 12A:
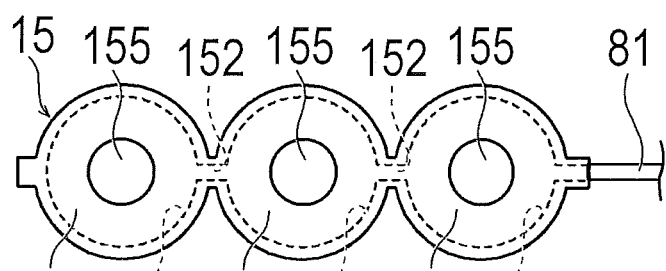
FIGS. 12(A) and 12(B) illustrate a seventh modified example of an inflation portion.
Figure 12B:
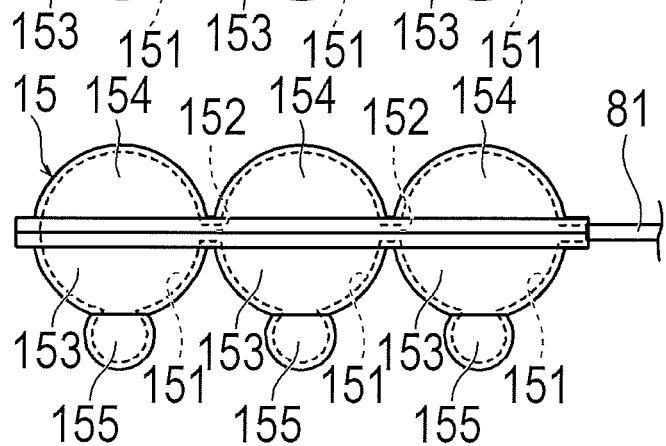

In addition, in an inflation portion 15 according to a seventh modified example illustrated in FIGS. 12(A) and 12(B), unitary spaces 151 which are circular when viewed from the wearing surface side may be formed so as to communicate with each other through a communicating section 152. When the inflation portion 15 inflates, the inflation portion 15 has a convex portion 153 formed in a shape in which a distal portion 155 serving as a sphere having a diameter smaller than the diameter of a hemisphere 156 is coupled with an apex of the hemisphere 156, on the wearing surface side. In addition, when the inflation portion 15 inflates, the inflation portion 15 has a support portion 154 which protrudes in a hemispherical shape, on the side opposite to the wearing surface side. The support portion 154 supports the convex portion 153 by coming into contact with the band 2, and performs a role of efficiently applying the compressive force to the blood vessel, thereby improving a hemostatic effect. A base portion of the distal portion 155 (on the wearing surface side) is formed to be thinly narrowed. Therefore, the convex portion 153 except for the distal portion 155 is less likely to come into contact with the body surface. Even if the convex portion 153 collapses after coming into contact with the body surface, a contact area is not greatly changed, and can always apply a proper compressive force.

Figure 13A:
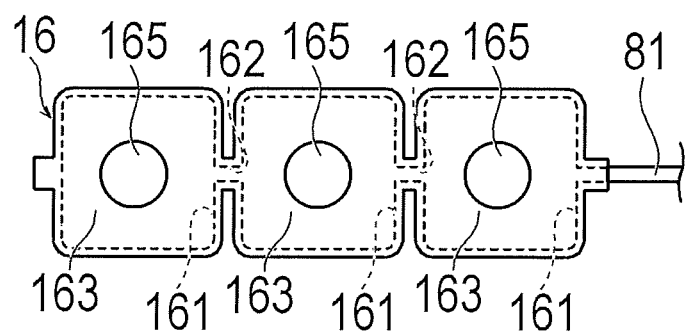
FIGS. 13(A) and 13(B) illustrate an eighth modified example of an inflation portion.
Figure 13B:
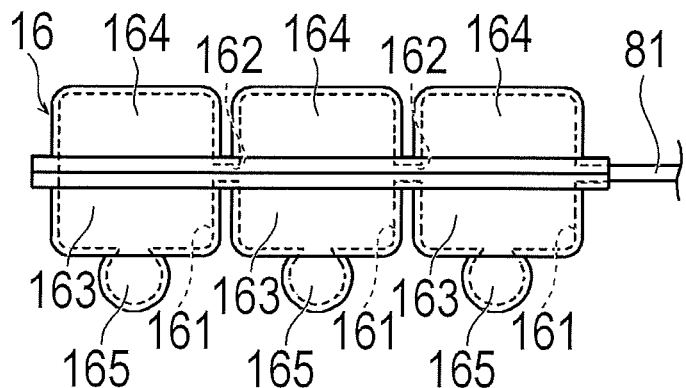

In addition, in an inflation portion 16 according to an eighth modification example illustrated in FIGS. 13(A) and 13(B), unitary spaces 161 which are substantially rectangular when viewed from the wearing surface side may be formed so as to communicate with each other through a communicating section 162. When the inflation portion 16 inflates, the inflation portion 16 has a convex portion 163 formed in a shape in which a spherical distal portion 165 is coupled with a prismatic apex of the rectangular convex portions 163, on the wearing surface side. In addition, when the inflation portion 16 inflates, the inflation portion 16 has a support portion 164 which protrudes in a prismatic shape, on the side opposite to the wearing surface side. The support portion 164 supports the convex portion 163 by coming into contact with the band 2, and performs a role of efficiently applying the compressive force to the blood vessel, thereby improving a hemostatic effect. A base portion of the distal portion 165 (on the wearing surface side) is formed to be thinly narrowed. Therefore, the convex portion 163 except for the distal portion 165 is less likely to come into contact with the body surface. Even if the convex portion 163 collapses after coming into contact with the body surface, a contact area is not greatly changed, and can always apply a proper compressive force.

Figure 14A:
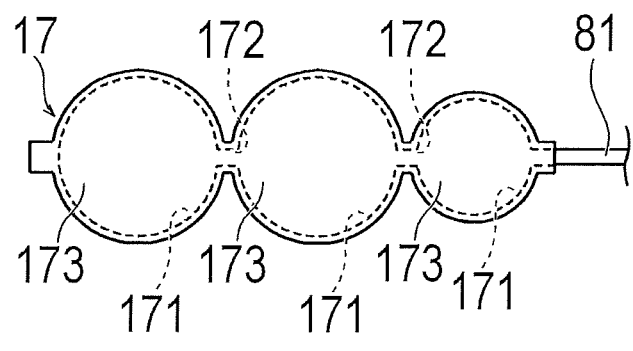
FIGS. 14(A) and 14(B) illustrate a ninth modified example of an inflation portion.
Figure 14B:
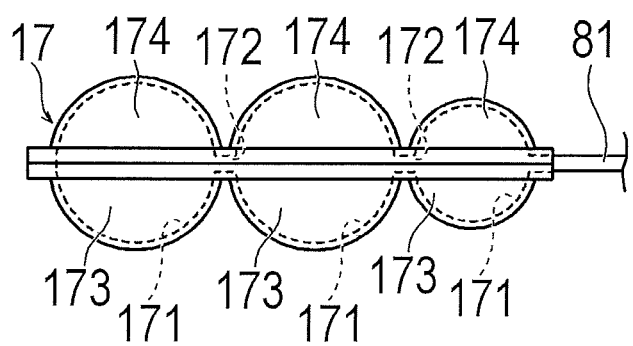

Further, in an inflation portion 17 according to a ninth modified example illustrated in FIGS. 14(A) and 14(B), a plurality of unitary spaces 171 which are circular when viewed from the wearing surface side may be formed so as to communicate with each other through a communicating section 172. At least one of the unitary spaces 171 may have a different diameter. When the inflation portion 17 inflates, the inflation portion 17 has a hemispherical convex portion 173 on the wearing surface side, and has a hemispherical support portion 174 which protrudes symmetrically with the convex portion 173, on the side opposite to the wearing surface side. The support portion 174 supports the convex portion 173 by coming into contact with the band 2, and performs a role of efficiently applying the compressive force to the blood vessel, thereby improving a hemostatic effect. In this way, a size of the convex portion 173 is changed to be different. Accordingly, it is possible to optionally set the compressive force generated by the convex portion 173, and it is possible to apply a proper compressive force to the body surface. For example, when the hemostatic device is worn on the limb, as illustrated in FIG. 14, in the inflation portion 17, the convex portion 173 having a large diameter is disposed on the heart side (side opposite to the side where the injector interlocks with the inflation portion 17 in the width direction of the band). In this manner, in an inflation portion 17, the compressive force of the convex portion 173 disposed on the upstream side of the blood vessel, which is closer to the heart and has higher blood pressure, can be stronger than the compressive force of the convex portion 173 disposed on the downstream side of the blood vessel. In this manner, in accordance with the blood pressure, the compressive force applied by the inflation portion 17 can be distributed in a well-balanced manner. Therefore, it is possible to achieve an excellent hemostatic effect while strain on a living body is reduced as much as possible without excessively inhibiting a blood flow.

Note that, in FIGS. 7(A), 7(B) and 13(A), 13(B), the inflation portion has the unitary spaces which are substantially rectangular when viewed from the wearing surface side. However, the shape of the unitary space is not limited to substantially the rectangular shape. For example, the inflation portion may have a polygonal unit space when viewed from the wearing surface side.

Figure 15:
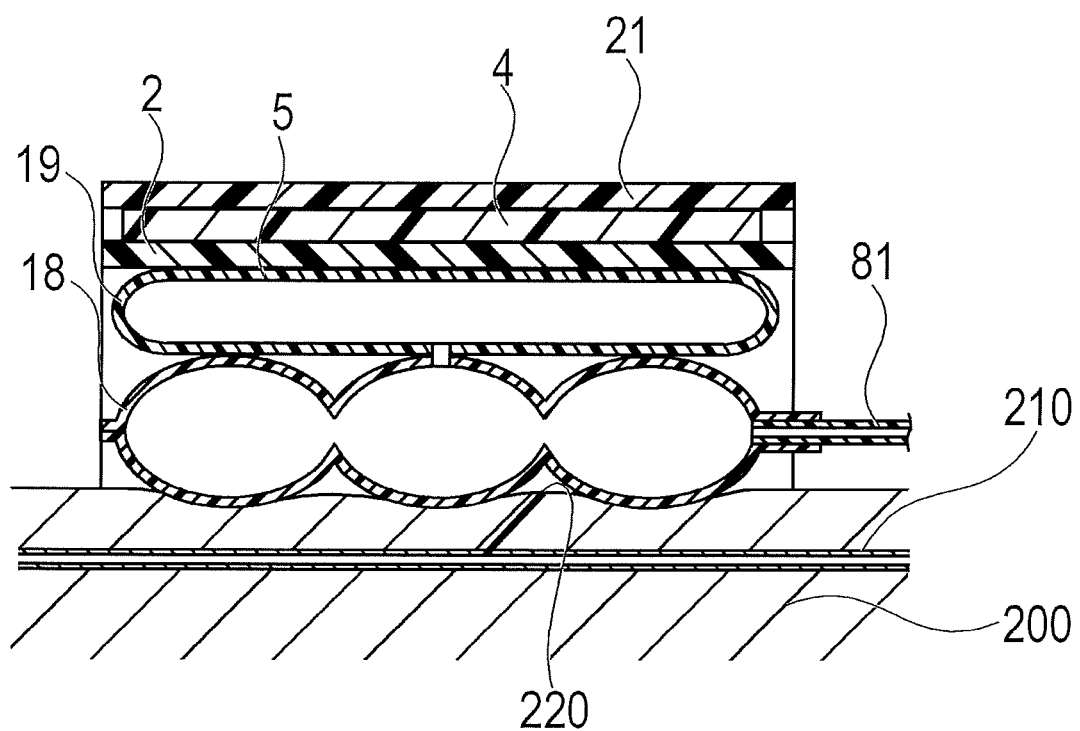
FIG. 15 is a longitudinal sectional view illustrating a tenth modified example of an inflation portion.

In addition, in a tenth modified example illustrated in FIG. 15, an auxiliary inflation portion 19 (pressing member) configured to include a flexible material may be disposed between the inflation portion 18 and the band 2 or the curved plate 4 so as to overlap the inflation portion 18. The auxiliary inflation portion 19 functions as a pressing member for pressing the inflation portion 18. The auxiliary inflation portion 19 communicates with the inflation portion 18, and inflates concurrently with the inflation portion 18 by injecting the fluid into the inflation portion 18. The auxiliary inflation portion 19 can easily adjust the compressing direction of the limb compressed by the inflation portion 18. Therefore, operability can be improved, and a hemostatic effect can be improved. Note that, the pressing member for pressing the inflation portion 18 is not limited to the auxiliary inflation portion 19. However, for example, the pressing member may be a pad-like member formed of a sponge-like substance, an elastic material, an aggregate of fibers such as cotton, or a combination thereof.

According to the disclosure herein, the number of convex portions of the inflation portion is not limited to three, and may be two or more. The number and the size of convex portions, or the position of the marker can be optionally set as desired according to the situation. In addition, the position of the marker may not be eccentrically disposed on one side in the width direction of the band, and may be disposed at the center in the width direction.

The detailed description above describes embodiments and modifications of a hemostatic device and method representing examples of the inventive hemostatic device and method disclosed here. The invention is not limited, however, to the precise embodiments and modifications described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
a flexible band configured to be wrapped around a hemostasis-requiring site of a limb;
a securing portion that secures the band in a state where the band is wrapped around the limb; and
an inflation portion configured to interlock with the band and inflate when a fluid is injected into the inflation portion,
wherein the inflation portion has a plurality of adjacent convex portions which are aligned with each other in a width direction orthogonal to a longitudinal direction of the band when the inflation portion is in an inflated state wherein the plurality of adjacent convex portions are defined by a plurality of unitary spaces.

2. The hemostatic device according to claim 1, further comprising:
a marker for aligning the inflation portion with the hemostasis-requiring site.

3. The hemostatic device according to claim 2, wherein the marker is disposed between the plurality of adjacent convex portions.

4. The hemostatic device according to claim 3, wherein the marker is eccentrically disposed on one side in the width direction of the band.

5. The hemostatic device according to claim 2, wherein the inflation portion is substantially transparent such that the marker can be aligned with the hemostasis-requiring site.

6. The hemostatic device according to claim 2, wherein the plurality of adjacent convex portions comprise three adjacent convex portions.

7. The hemostatic device according to any one of claim 1, further comprising:
a curved plate formed of a material harder than that of the band,
wherein the band holds the curved plate so as to overlap the inflation portion.

8. The hemostatic device according to claim 7, further comprising:
a pressing member provided between the curved plate and the inflation portion so as to press the inflation portion,
wherein the pressing member is disposed so as to overlap the inflation portion.

9. The hemostatic device according to claim 1, wherein the plurality of unitary spaces are in fluid communication with one another through a communicating section.

10. The hemostatic device according to claim 1, wherein the plurality of unitary spaces are substantially circular.

11. The hemostatic device according to claim 1, wherein the plurality of unitary spaces are substantially rectangular.

12. A hemostatic device comprising:
a band adapted to be wrapped around a limb of a patient at a site on the limb where bleeding is to be stopped;
securing means for securing the band in a wrapped state around the limb;
an inflation portion disposed on an inner peripheral surface of the band, and adapted to be inflated by injecting a fluid; and
an injection portion adapted to inject the fluid into the inflation portion,
wherein the inflation portion includes a plurality of adjacent convex portions configured to be aligned with each other in a width direction orthogonal to a longitudinal direction of the band when the inflation portion is in an inflated state wherein the plurality of adjacent convex portions are defined by a plurality of unitary spaces.

13. The hemostatic device according to claim 12, wherein the plurality of adjacent convex portions are circular.

14. The hemostatic device according to claim 12, wherein the plurality of adjacent convex portions are rectangular.

15. The hemostatic device according to claim 12, further comprising:
a marker for aligning the inflation portion with the site on the limb where bleeding is to be stopped, the marker being disposed between a first and a second of the plurality of adjacent convex portions.

16. The hemostatic device according to claim 15, wherein the marker is eccentrically disposed on one side in the width direction of the band.

17. A method for performing hemostasis on a puncture site of a blood vessel of a patient's limb, the method comprising:
securing a band of a hemostatic device on a patient's limb, the hemostatic device including the band for being wrapped around the limb of the patient at a site on the limb where bleeding is to be stopped, securing means for securing the band in a state where the band is wrapped around the limb, an inflation portion that interlocks with the band, and that is inflated by injecting gas, the inflation portion including a plurality of adjacent convex portions configured to be aligned with each other in a width direction orthogonal to a longitudinal direction of the band when the inflation portion is in an inflated state, and a marker disposed between the plurality of adjacent convex portions;

aligning the marker disposed between the plurality of adjacent convex portions with the puncture site so that the inflation portion covers the puncture site;

injecting a gaseous substance into the inflation portion to inflate the inflation portion; and in a state where the inflation portion is inflated, applying a compressing force to the blood vessel by the convex portions of the inflation portion.

18. The method for performing hemostasis according to claim 17, wherein applying the compressing force to the blood vessel includes applying the compressing force to an upstream side of the blood vessel from the puncture site and applying the compressing force to a downstream side of the blood vessel from the puncture site.

19. The method for performing hemostasis according to claim 18, wherein the compressing force to the upstream side of the blood vessel from the puncture site is greater than the compressing force to the downstream side of the blood vessel from the puncture site.

* * * * *